United States Patent [19]

Brown et al.

[11] Patent Number: 4,681,883

[45] Date of Patent: Jul. 21, 1987

[54] HISTAMINE $H_2$-ANTAGONIST OXAZOLE AND THIAZOLE DERIVATIVES AND COMPOSITIONS THEREFOR

[75] Inventors: Thomas H. Brown, Tewin; Robert C. Mitchell, Hertford; Ian R. Smith, Knebworth; Rodney C. Young, Bengeo, all of England

[73] Assignee: Smith Kline & French Laboratories Limited, Welwyn Garden City, England

[21] Appl. No.: 788,261

[22] Filed: Oct. 17, 1985

[30] Foreign Application Priority Data

Nov. 3, 1984 [GB] United Kingdom ................. 8427878
Jul. 13, 1985 [GB] United Kingdom ................. 8517714

[51] Int. Cl.⁴ .................. A61K 31/42; A61K 31/425; C07D 413/12; C07D 417/12
[52] U.S. Cl. .................................... 514/212; 514/321; 514/326; 514/367; 514/370; 514/375; 514/377; 540/524; 546/198; 546/209; 548/161; 548/173; 548/222; 548/233

[58] Field of Search ................ 540/524; 546/198, 209; 548/161, 193, 222, 233; 514/212, 321, 326, 367, 370, 375, 377

[56] References Cited

U.S. PATENT DOCUMENTS

| | | | |
|---|---|---|---|
| 4,439,437 | 3/1984 | Jones et al. | 546/261 |
| 4,447,611 | 5/1984 | Klaubert et al. | 546/118 |
| 4,490,527 | 12/1984 | Schiehser et al. | 544/62 |
| 4,496,567 | 1/1985 | Brown et al. | 514/272 |
| 4,521,418 | 6/1985 | Brown et al. | 544/320 |
| 4,524,071 | 6/1985 | Price et al. | 544/320 |

FOREIGN PATENT DOCUMENTS 143630A 6/1985 European Pat. Off. ............ 514/272

Primary Examiner—Henry R. Jiles
Assistant Examiner—J. G. Mullins
Attorney, Agent, or Firm—Linda E. Hall; Stuart R. Suter; Alan D. Lourie

[57] ABSTRACT

This invention relates to aminoalkylphenoxyalkyl substituted heterocycles. These compounds antagonize the action of histamine on histamine $H_2$-receptors in the brain. A compound of the invention is 2-[3-[3-(piperidinomethyl)phenoxy]propylamino]benzthiazole.

19 Claims, No Drawings

HISTAMINE H₂-ANTAGONIST OXAZOLE AND THIAZOLE DERIVATIVES AND COMPOSITIONS THEREFOR

This invention relates to heterocyclic derivatives, pharmaceutical compositions containing them, and a method of blocking histamine H₂-receptors in the brain by administering them.

Histamine, a physiologically active compound endogenous in mammals, exerts its action by interacting with certain sites called receptors. One type of receptor is known as a histamine H₁-receptor (Ash and Schild, Brit. J. Pharmac. Chemother. 27 427 (1966)) and the actions of histamine mediated through these receptors are blocked by drugs commonly called "antihistamines" (histamine H₁-antagonists) a common example of which is mepyramine. A second type of histamine receptor is known as the H₂-receptor (Black et al. Nature 1972, 236, 385). These receptors are not blocked by mepyramine but are blocked by burimamide. Compounds which block these histamine H₂-receptors are called histamine H₂-antagonists.

Histamine H₂-antagonists are useful in treating disease conditions caused by the biological effects of histamine mediated through H₂-receptors, for example, as inhibitors of gastric acid secretion, in the treatment of inflammation mediated through histamine H₂-receptors and as agents which act on the cardiovascular system, for example, as inhibitors of effects of histamine on blood vessels and heart mediated through histamine H₂-receptors.

Cimetidine is an example of a histamine H₂-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In addition to the biological effects of histamine outlined above, histamine has been implicated in neuronal and vascular functions in the brain. Thus the presence of histamine, the histamine synthesizing enzyme histidine decarboxylase and the histamine catabolizing enzyme histamine N-methyl transferase have been demonstrated in the brain of various species including man. Histamine may be localised in neurones, brain mast cells and blood vessels. Further, the presence of histamine H₂-receptors in the brain and on the cerebral vasculature has been demonstrated pharmacologically in various species. Currently available histamine H₂-receptor antagonists are not very lipophilic and are not able to penetrate the blood-brain barrier to a significant extent, and are therefore unable to act on central H₂-receptors. Additionally, this might have limited their usefulness in treating some peripheral conditions other than secretion of gastric acid which are mediated through H₂-receptors.

The present invention provides compounds that have histamine H₂-receptor antagonist activity and have relatively high lipophilicity. Specifically they have the ability to penetrate the blood-brain barrier and antagonise the action of histamine on histamine H₂-receptors in the brain. Therefore these compounds would be of use in clinical conditions mediated by histamine H₂-receptors in the brain. Because of their ability to penetrate tissues, they are also likely to be of greater effectiveness than conventional histamine H₂-receptor antagonists in treating peripheral conditions other than the secretion of gastric acid which are mediated through histamine H₂-receptors in the eye, skin or bowel e.g. skin inflammation, burns, ocular inflammation, elevated intraocular pressure and inflammatory bowel disease.

In brain, one such clinical condition is vascular headache, specifically migraine and cluster headache. Vascular headache has been considered to arise from dilatation of the main cerebral arteries and their branches overlying the surface of the brain. Histamine has been shown both in vitro and in situ to dilate these arteries via stimulation of histamine H₂-receptors (see, for example, Edvinsson et al., J. Pharmac. Exp. Ther. 225 168-175 (1983)). In the clinical situation the histamine involved and its receptors would be situated on the brain side of the blood-brain barrier. Non-brain penetrating histamine H₂-receptor antagonists such as cimetidine would not be expected to antagonise this action of locally applied histamine following systemic administration, whereas brain-penetrating histamine H₂-receptor antagonists would. This has been confirmed using the in situ pial artery technique in cats. Blockade of these histamine receptors by a brain-penetrating histamine H₂-receptor antagonist would therefore be predicted to be of value in combatting vascular headache.

Another disease condition in which cerebral histamine may be implicated is epilepsy. Known anticonvulsant drugs such as phenytoin sodium antagonise experimental convulsions in mice induced by maximal electroshock (MES), leptazol (pentylenetetrazol) injection or bicuculline injection. Some of the brain penetrating histamine H₂-receptor antagonists of this invention have also been shown to be active in these tests, which are indicative of therapeutic use in clinical conditions where anticonvulsant drugs are indicated. Anticonvulsant therapy is commonly performed using a combination of drugs. Therefore combination therapy with other anticonvulsant drugs is predicted to be of value.

Aminoheterocyclic derivatives are known from U.S. Pat. No.4,447,611 assigned to American Home Products inter alia having the formula :

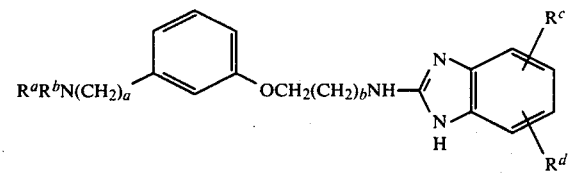

wherein $R^a$ and $R^b$ are hydrogen, lower alkyl, cycloloweralkyl, or together form a nitrogen containing heterocycle; a and b are independently 1 to 5; and $R^c$ $R^d$ independently hydrogen, lower alkyl, lower alkoxy, halogen or thioalkyl. These compounds are described for use in the treatment of conditions where there is hypersecretion of gastric acid, such as in gastric and peptic ulceration, and other conditions caused or exacerbated by gastric acidity such as stress ulceration or gastric intestinal bleeding due to trauma.

There is no suggestion in the U.S. Patent that the compounds of the above formula have a use in the treatment of therapeutic conditions wherein blocking of histamine H₂-receptors in the brain is thought to be beneficial, or that any of the compounds are lipophilic or might be particularly useful because of their lipophilic properties which affects their distribution throughout the body.

We have discovered compounds that possess histamine H$_2$-antagonist activity and are significantly lipophilic and have a significant ability to penetrate the blood- brain-barrier. Thus they are indicated for use in the treatment of therapeutic conditions wherein such properties would be beneficial.

Accordingly the present invention provides a compound of formula (I):

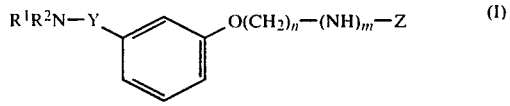

or a pharmaceutically acceptable salt thereof, wherein:
R$^1$ and R$^2$ are independently C$_{1-4}$alkyl; or R$^1$ and R$^2$ together with the nitrogen atom to which they are joined represent a pyrrolidino, piperidino or hexahydroazepino ring;
Y is straight-chain or branched-chain C$_{1-4}$alkyl;
n is 2 to 5;
m is 0 or 1;
when m is 1, Z is a group of sub-formula (a) or (b):

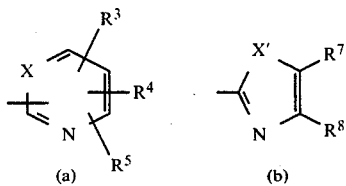

wherein
x is N or CR$^6$;
X' is oxygen, NR$^9$ or sulphur;
R$^3$-R$^8$ are independently hydrogen, C$_{1-6}$alkyl, phenyl, benzyl, halo, benzyloxy or C$_{1-6}$alkoxy;
R$^9$ is hydrogen or C$_{1-6}$alkyl; or
any two of R$^3$-R$^8$ on adjacent atoms may be joined to form a benzene ring; said benzene ring being optionally substituted by up to 3 moieties selected from C$_{1-6}$alkyl, C$_{1-6}$alkoxy, halo, phenyl, benzyl or benzyloxy:
with the proviso that R$^9$ is not hydrogen when R$^7$ and R$^8$ are joined to form a benzene ring:
and with the further proviso that when X' is oxygen R$^7$ and R$^8$ are independently hydrogen, C$_{1-6}$alkyl, phenyl or benzyl, or are joined to form an optionally substituted benzene ring;
when m is 0, Z is a group of sub-formula (c):

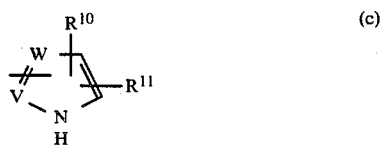

wherein:
one of V and W is N and the other is C; R$^{10}$ and R$^{11}$ are independently hydrogen, C$_{1-6}$alkyl, phenyl, benzyl, C$_{1-6}$alkoxy and halo;
or when W is N and the —O(CH$_2$)$_n$—chain is attached to V, and R$^{10}$ and R$^{11}$ may be joined to form a benzene ring; said benzene ring being optionally substituted by one to three moieties selected from C$_{1-6}$alkyl, C$_{1-6}$alkoxy, halo, phenyl and benzyl.

Suitably R$^1$ is methyl, ethyl or n-propyl. Suitably R$^2$ is methyl, ethyl or n-propyl. In a preferred aspect R$^1$ and R$^2$ are the same, in particular R$^1$R$^2$N— is dimethylamino.

In another preferred aspect R$^1$R$^2$N— is pyrrolidino or piperidino, in particular piperidino.

Suitably Y is methylene.
n is 2 to 5, suitably 3 or 4.
m is 0 or 1.
Preferably n is 3 when m is 1, preferably n is 4 when m is 0.

Suitably Z is a group of sub-formula (a), thus forming a pyrimidine or pyridine moiety, for example a pyrimidin-2-yl, pyrimidin-4-yl, pyrid-2-yl, pyrid-3-yl or pyrid-4-yl moiety. Preferably Z is pyrimidin-2-yl or pyrid-2-yl. Suitably R$^3$-R$^6$ are independently hydrogen, C$_{1-6}$alkyl for example methyl or ethyl, C$_{1-6}$alkoxy for example methoxy or ethoxy, or halo for example fluoro, bromo or chloro. More suitably R$^3$-R$^6$ are independently hydrogen or methyl.

In an another aspect two of R$^3$-R$^6$ on adjacent carbon atoms are joined to form a benzene ring, for example forming a quinoline, isoquinoline or quinazoline ring system. Preferably Z is quinolin-2-yl.

Suitably Z is a group of sub-formula (b), thus forming an imidazole or thiazole moiety. Preferably Z is thiazol-2-yl. Suitably R$^7$ and R$^8$ are independently hydrogen, C$_{1-6}$alkyl for example methyl or ethyl, C$_{1-6}$alkoxy for example methoxy or ethoxy, or halo for example fluoro, bromo or chloro. More suitably R$^7$ and R$^8$ are independently hydrogen or methyl. Suitably R$^9$ is hydrogen, methyl or ethyl.

In an another aspect R$^7$ and R$^8$ are joined to form a benzene ring forming a benzimidazol-2-yl, benzothiazol-2-yl or benzoxazol-2-yl ring system. Suitable substituents for said benzene ring include C$_{1-6}$alkyl such as methyl or ethyl, C$_{1-6}$alkoxy such as methoxy or ethoxy, or halo for example chloro, bromo or fluoro.

Suitably Z is a group of sub-formula (c) and V is N and W is C, thus forming a pyrazole ring system. Suitable substituents for such a ring system are hydrogen, C$_{1-6}$alkyl, for example methyl or ethyl, or hale for example chloro or bromo.

More suitably V is C and W is N thus forming an imidazole ring system. Suitable substituents for such a ring system are hydrogen, C$_{1-6}$alkyl for example methyl or ethyl, C$_{1-6}$alkoxy for example methoxy or ethoxy, or halo for example chloro or bromo. In a preferred alternative the —O(CH$_2$)$_n$— chain is attached to V, and R$^{10}$ and R$^{11}$ together with the carbon atoms to which they are joined form a benzene ring, thus forming a benzimidazole ring system. Suitable substituents for the benzene ring are hydrogen, C$_{1-6}$alkyl for example methyl or ethyl, C$_{1-6}$alkoxy for example methoxy or ethoxy, or halo for example chloro, bromo or fluoro.

Preferably V is C, W is N, the —O(CH$_2$)$_n$— chain is attached to V and and R$^{10}$ and R$^{11}$ are joined to form a benzene ring which is unsubstituted.

Particular compounds of this invention are:
2-[3-[3-(piperidinomethyl)phenoxy]propylamino]benzoxazole,
2-[3-[3-(piperidinomethyl)phenoxy]propylamino]-3-chloro- pyridine,
2-[3-[3-(piperidinomethyl)phenoxy]propylamino]quinoline, 2-[3-[3-(piperidinomethyl)phenoxy]propylamino]-pyrimidine,
2-[3-[3-(piperidinomethyl)phenoxy]propylamino]benzthiazole,
2-[3-[3-(piperidinomethyl)phenoxy]propylamino]pyridine,
2-[3-[3-(piperidinomethyl)phenoxy]propylamino]-6-methoxy- pyridine,
2-[3-[3-(piperidinomethyl)phenoxy]propylamino]-4-ethoxy- quinoline,
2-[3-[3-(piperidinomethyl)phenoxy]propylamino]-thiazole,
2-[3-[3-(piperidinomethyl)phenoxy]propylamino]-1-methyl- benzimidazole,
3-[3-[3-(piperidinomethyl)phenoxy]propylamino]pyridine,
1-[3-[3-(piperidinomethyl)phenoxy]-propylamino]isoquinoline,
2-[3-[3-(piperidinomethyl)phenoxy]propylamino]-4,5-dimethyl- thiazole,
2-[5-[3-(piperidinomethyl)phenoxy]pentylamino]benzthiazole,
2-[2-[3-(piperidinomethyl)phenoxy]ethylamino]benzthiazole,
2-[4-[3-(piperidinomethyl)phenoxy]butylamino]benzthiazole,
2-[3-[3-(piperidinomethyl)phenoxy]propylamino]-3-methoxy- pyridine,
4-[3-[3-(piperidinomethyl)phenoxy]propylamino]-quinazoline,
4-[3-[3-(piperidinomethyl)phenoxy]propylamino]quinoline,
2-[3-[3-(dimethylaminomethyl)phenoxy]propylamino]-benzthiazole,
2-[3-[3-(pyrrolidinomethyl)phenoxy]propylamino]benzthiazole,
2-[3-[3-(hexahydroazepinomethyl)phenoxy]-propylamino]- benzthiazole,
2-[3-[3-(piperidinomethyl)phenoxy]propylamino]-5,6-dimethyl- benzthiazole,
4(5)-[2-[3-(piperidinomethyl)phenoxy]ethyl]imidazole,
2-[2-[3-(piperidinomethyl)phenoxy]ethyl]-1H-benzimidazole,
2-[3-[3-(piperidinomethyl)phenoxy]propyl]-1H-benzimidazole, and
2-[4-[3-(piperidinomethyl)phenoxy]butyl]-1H-benzimidazole
and pharmaceutically acceptable salts thereof.

Suitable pharmaceutically acceptable salts of the compounds of the formula (I) include pharmaceutically acceptable acid addition salts, for example those formed with hydrochloric, hydrobromic, sulphuric, phosphoric, acetic, citric, maleic, lactic, ascorbic, fumaric, oxalic, methanesulphonic and ethanesulphonic acids.

In order to use the compounds of the formula (I) or pharmaceutically acceptable salts thereof for medical purposes, they are normally formulated in accordance with standard pharmaceutical practice as pharmaceutical compositions.

The invention further provides pharmaceutical compositions for blocking histamine H₂-receptors in the brain which comprises an effective amount of a compound of the formula (I) or a pharmaceutically acceptable salt thereof and a pharmaceutically acceptable carrier.

The compositions of this invention are normally formulated in accordance with standard pharmaceutical practice. They may be administered, for example orally, parenterally, trans-dermally, rectally or via inhalation or insufflation.

The compounds of the formula (I) and their pharmaceutically acceptable salts which are active when given orally can be formulated as syrups, tablets, capsules and lozenges. A syrup formulation will generally consist of a suspension or solution of the compound or pharmaceutically acceptable salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or pharmaceutically acceptable salt in a sterile aqueous carrier or parenterally acceptable oil, for example polyvinylpyrrolidine, lecithin, polyethyleneglycol, arachis oil, syrup, water, ethanol, peanut oil and olive oil.

A typical suppository formulation comprises a compound or pharmaceutically acceptable salt thereof, which is active when administered in this way, with a binding and/or lubricating agent such as gelatin or cocoa butter or other low melting vegetable waxes or fats.

Typical compositions for inhalation or insufflation are in the form of an aerosol with a conventional propellant, such as dichlorodifluoromethane or trichlorofluoromethane.

Typical transdermal formulations comprise of a conventional aqueous or non-aqueous vehicle, for example a cream, ointment, lotion or paste or in the form of a medicated plaster, patch or membrane.

Preferably the composition is in unit dose form such as a tablet or capsule.

Each dosage unit for oral administration contains preferably from 10 to 1000 mg (and for parenteral administration contains preferably from 1.0 to 100 mg) of a compound of the formula (I) or a pharmaceutically acceptable salt thereof calculated as the free base. For administration by inhalation or insufflation dosages are controlled by a valve and are conveniently in the range 0.1–5.0 mg of a compound of the formula (I) or a pharmaceutically acceptable salt thereof.

The invention also provides a method of blocking histamine H₂-receptors in the brain which comprises administering to an animal an effective amount to block said receptors of a compound of the formula (II) or a pharmaceutically acceptable salt thereof:

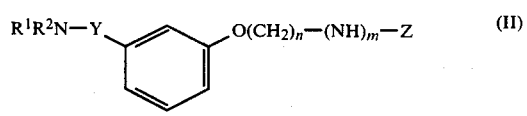
(II)

or a pharmaceutically acceptable salt thereof, wherein:
$R^1$ and $R^2$ are independently $C_{1-4}$alkyl; or $R^1$ and $R^2$ together with the nitrogen atom to which they are joined represent a pyrrolidino, piperidino or hexahydroazepino ring;
Y is straight-chain or branched-chain $C_{1-4}$alkyl;
n is 2 to 5;
m is 0 or 1,
when m is 1, Z is a group of sub-formula (a) or (b):

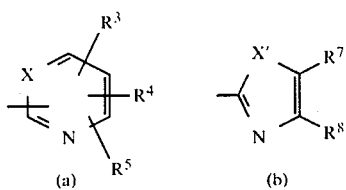

wherein
- X is N or $CR^6$;
- X' is oxygen, $NR^9$ or sulphur;
- $R^3$–$R^8$ are independently hydrogen, $C_{1-6}$alkyl, phenyl, benzyl, halo, benzyloxy or $C_{1-6}$alkoxy;
- $R^9$ is hydrogen or $C_{1-6}$alkyl; or
- any two of $R^3$–$R^8$ on adjacent atoms may be joined to form a benzene ring; said benzene ring being optionally substituted by up to 3 moieties selected from $C_{1-6}$alkyl, $C_{1-6}$alkoxy, halo, phenyl, benzyl or benzyloxy:

and with the proviso that when X' is oxygen $R^7$ and $R^8$ are independently hydrogen, $C_{1-6}$alkyl, phenyl or benzyl, or are joined to form an optionally substituted benzene ring;

when m is 0, Z is a group of sub-formula (c):

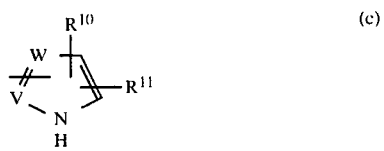

wherein:
- one of V and W is N and the other is C; $R^{10}$ and $R^{11}$ are independently hydrogen, $C_{1-6}$alkyl, phenyl, benzyl, $C_{1-6}$alkoxy and halo;
- or when W is N and the $-O(CH_2)_n-$ chain is attached to V, and $R^{10}$ and $R^{11}$ may be joined to form a benzene ring; said benzene ring being optionally substituted by one to three moieties selected from $C_{1-6}$alkyl, $C_{1-6}$alkoxy, halo, phenyl and benzyl.

It can be seen that this aspect of the invention encompasses some compounds of the above mentioned U.S. Pat. as such a method of treatment is not suggested therein. The compounds of the formula (II) can be made and used in the same manner as the compounds of the formula (I).

The compounds of formula (II) or a pharmaceutically acceptable salt thereof will normally be administered to a subject to block histamine $H_2$-receptors in the brain and particularly for the treatment of vascular headache and/or other cerebral conditions caused or exacerbated by histamine. The daily dosage regimen for example for an adult patient may be an oral dose of between 10 mg and 1000 mg, preferably between 50 mg and 500 mg, or an intravenous, subcutaneous, or intramuscular dose of between 10 mg and 500 mg, preferably between 20 mg and 50 mg, of the compound of the formula (I) or a pharmaceutically acceptable salt thereof calculated as the free base, the compound being administered 1 to 6 times per day. A conveniently daily dosage for administration by inhalation or insufflation is in the range 0.1–100 mg with an appropriate number of doses administered during the day.

The compounds of formula (II) or a pharmaceutically acceptable salt thereof may also be administered for the treatment of conditions mediated through $H_2$-receptors in the eye, skin and bowel where a lipophilic compound is necessary to achieve effective distribution, e.g. skin inflammation, burns, ocular inflammation, elevated intraocular pressure, and inflammatory bowel disease.

The compounds of the formula (I) and salts thereof may be prepared by a process which comprises:

(a) for compounds in which m is 1 other than those wherein X' is oxygen and $R^7$ and $R^8$ are not joined to form a benzene ring, reacting a compound of the formula (III) with a compound of the formula (IV):

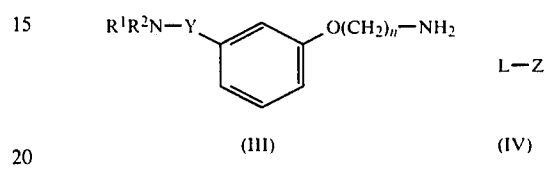

wherein $R^1$, $R^2$, Y, n and Z are as hereinbefore defined and L is a group displaceable by an amine; or (b) reacting a compound of the formula (V) or a chemical equivalent thereof with a compound of the formula (VI):

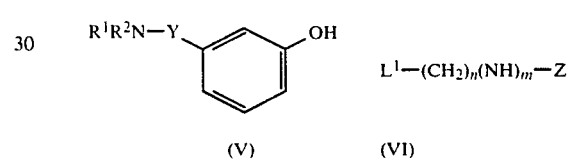

wherein $R^1$, $R^2$, Y, n, m and Z are as hereinbefore defined and $L^1$ is a moiety displaceable by phenol or chemical equivalent thereof; or (c) converting a compound of the formula (VII):

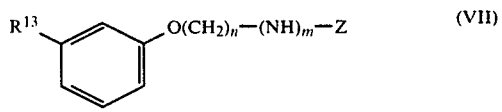

wherein n, m and Z are as hereinbefore defined and $R^{13}$ is a precursor of a group $R^1R^2N-Y-$ as hereinbefore defined (d) for compounds wherein m is 1 reducing a compound of the formula (VIII):

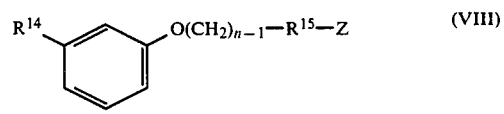

wherein n and Z are as hereinbefore defined, $R^{14}$ is a group $R^1R^2N-Y-$ or $R^{13}$ as hereinbefore defined, and $R^{15}$ is a group $-CH=N$ or $-CONH-$;

(e) for compounds wherein m is 1, X' is oxygen and $R^7$ and $R^8$ are not joined to form a benzene ring, reacting a compound of the formula (IX) with a compound of the formula (X):

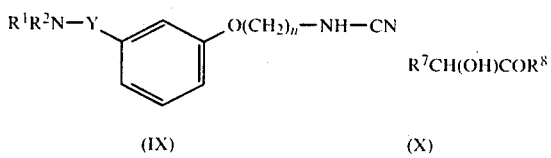

(IX)    (X)

wherein $R^1$, $R^2$, Y, n, $R^7$ and $R^8$ are as hereinbefore defined;

(f) for compounds wherein m is 1 and X is CH reducing a compound of the formula (XI):

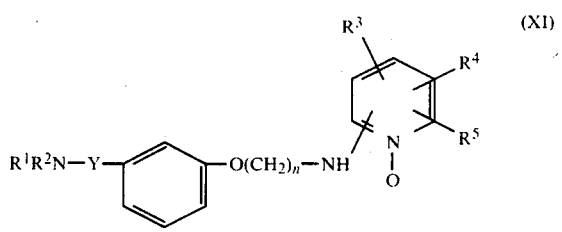

wherein $R^1$, $R^2$, Y, n, $R^3$, $R^4$ and $R^5$ are as hereinbefore defined; or (g) for compounds wherein m is 0, W is N, V is C, the $-O(CH_2)_n-$ chain is attached to V, and $R^{10}$ and $R^{11}$ are joined to form an optionally subtituted benzene ring, reacting a compound of the formula (XII) and optionally substituted ortho-phenylenediamine:

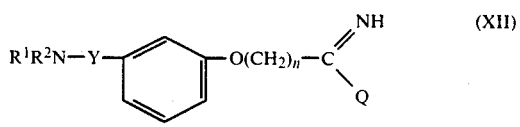

wherein $R^1$, $R^2$, Y and n are as hereinbefore defined and Q is a displaceable group;

and thereafter, if desired, forming a pharmaceutically acceptable salt.

Suitably L is $C_{1-6}$alkylthio, benzylthio, chloro or bromo. Of these chloro is preferred.

The reaction between a compound of the formula (III) and a compound of formula (IV) can be performed, under a variety of conditions depending on the nature of the compound of the formula (IV). For example the reaction may be performed for example in the absence of solvent at 120°–170° C., or the reaction may be performed in a substantially inert solvent for example in a $C_{1-6}$alkanol, pyridine or anisole, at a temperature between $-10°$ C. and 140° C.

In the reaction between the compounds of the formulae (V) and (VI) suitably $L^1$ is chloro or bromo. Suitably the reaction is performed under basic conditions, for example the anion of the compound of the formula (V) may be generated, for example using sodium hydride or an alkali or alkaline earth metal carbonate. The reaction is performed in a suitable aprotic solvent for example dimethylformamide or acetone at a non-extreme temperature for example between 0° C. and 100° C., suitably between ambient and 70° C.

In the compounds of the formulae (VII) and (VIII) in one suitable aspect $R^{13}$ is a group $R^1R^2N(CH_2)_xCO(CH_2)_y-$ wherein $x+y=$ zero to 3. Favourably x and y are both zero so that the group $R^1R^2NCO-$ is a precursor to the group $R^1R^2NCH_2-$. The conversion of such a group $R^1R^2N(CH_2)_xCO(CH-$ $2)_y-$ may be performed by reduction for example with a hydride for example lithium aluminium hydride.

In an alternative aspect $R^{13}$ is a group $-CHO$ or $-$alkylene$-CHO$, which may be converted to a group $R^1R^2N-Y-$ on reaction with an amine $R^1R^2NH$ under conditions of reductive amination. Optionally the aldehyde group can be protected as acetal or cyclic acetal derivative. In another suitable aspect $R^{13}$ may be a group HO$-Y-$ which may be converted directly to $R^1R^2N-Y-$ or indirectly thereto for example via a moiety such as Br$-Y-$ and thence to $R^1R^2N-Y-$. Such transformations may be carried out in conventional manner.

The compounds of the formula (VIII) may be carefully reduced to form compounds of the formula (I), for example using lithium aluminium hydride in an ether solvent when $R^{15}$ is $-$CONH$-$; and for example using a borohydride in an alkanol, lithium aluminium hydride in an ether solvent, or catalytically hydrogenating when $R^{15}$ is $-CH=N-$.

The compounds of the formula (IX) and (X) can be reacted in conventional manner, for example in aqueous solution at ambient to 100° C., in the presence of a mineral acid catalyst, or preferably in the presence of a basic catalyst, for example sodium hydroxide, at ambient to 100° C., for example 40°–60° C.

The N-oxides of the formula (XI) can be reduced in conventional manner. In a preferred aspect the reduction is performed using phosphorus tribromide.

In the reaction between optionally substituted ortho-phenylenediamine and a compound of the formula (XII) suitably Q is $C_{1-4}$alkoxy for example methoxy or ethoxy. The reaction is performed in a substantially inert solvent, for example a $C_{1-4}$alkanol, at a non-extreme temperature, conveniently ambient.

In the processes of this invention the $-NH-$ group on the heterocycle, if desired, can be optionally protected. Suitable protecting groups are those conventional in the art, for example see "Protective Groups in Organic Synthesis", T. W. Greene 1981 (Wiley). Such protecting groups should be readily removable by hydrogenation or hydrolysis and include, for example, p-toluenesulphonyl, trityl, t-butoxycarbonyl and benzyloxycarbonyl.

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

The compounds of the formula (III) may be prepared by methods known to the art for example by the methods of U.S. Pat. Nos. 4,496,567; 4,521,418; and 4,524,071. The compounds of the formula (VI) in which m is 1 may be prepared by the reaction of a corresponding compound of formula (IV) with an aminoalkanol and, subsequently converting a hydroxy group to a group $L^1$. The compounds of the formula (IX) can be prepared by reaction of a compound of the formula (III) and cyanogen bromide.

The compounds of the formula (VII) may be prepared in a manner analogous to that described for the preparation of compounds of the formula (I), for example reacting a compound of the formula (VI) with an analogue of the formula (V) wherein $R^1R^2N\text{-}Y\text{-}$ is replaced by $R^{13}$, provided that $R^{13}$ is suitably protected as necessary.

The compounds of the formula (VIII) wherein $R^{15}$ is CH=N may be prepared by the reaction of a compound of the formula (XIII) with a compound of the formula (XIV):

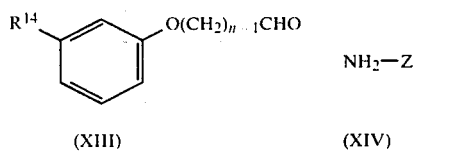

wherein $R^{14}$, n and Z are as hereinbefore defined, optionally in the presence of an acid catalyst. The compounds of the formula (VIII) wherein $R^{15}$ is —CONH— may be prepared by the reaction of a compound of the formula (XIV) with an activated derivative of a compound of the formula (XV):

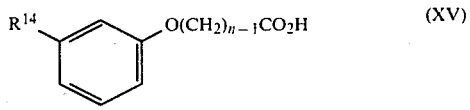

wherein $R^{14}$ and n are as hereinbefore defined. Suitable active derivatives are acyl halides, anhydrides and activated esters. The aldehydes of the formula (XIII) and the acids of the formula (XV) and derivatives thereof may be prepared in a conventional manner.

The compounds of the formula (XI) can be prepared by methods analogous to those described for preparing compounds of the formula (I). Suitably $R^3$ is benzyloxy or $C_{1-6}$alkoxy in a position para to the N-O moiety. For example a compound of the formula (III) can be reacted with a compound of the formula (XVI):

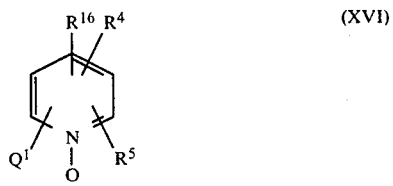

wherein $Q^1$ is a leaving group, e.g. chloro or bromo, $R^4$ and $R^5$ are as hereinbefore defined and $R^{16}$ is a group $R^3$ or a group convertible thereto, e.g. nitro which is convertible to benzyloxy or $C_{1-6}$alkoxy; and thereafter, where appropriate, converting $R^{16}$ to a group $R^3$ as hereinbefore defined.

The compounds of the formula (XII) may be prepared by methods known in the art. In particular compounds wherein Q is $C_{1-4}$alkoxy are known to the art or are preparable by known methods for example by the methods of EP-A-87274 and EP-A-50407.

The following Examples and Description serve to illustrate this invention.

EXAMPLE 1

2-[3-[3-(Piperidinomethyl)phenoxy]propylamino]benzoxazole

To 3-[3-(piperidinomethyl)phenoxy]propylamine (0.28 g) and triethylamine (0.40 g) in ethanol (2 ml), at 0° C., under nitrogen, was added 2-chlorobenzoxazole (0.17 g). The reaction mixture was stirred for one hour at 0° C., stirred at room temperature for 16 hours, evaporated under reduced pressure and subjected to column chromatography on silica (chloroform:methanol 25:1) to give the title compound as an oil (0.35 g). This was treated with anhydrous oxalic acid (2.1 equivalents) in methanol (5 ml). Addition of diethyl ether gave 2-[3-[3-(piperidinomethyl)phenoxy]propylamino]benzoxazole dioxalate (0.245 g), m.p. 172°-$\frac{1}{4}$° C. (recrystallised from isopropanol-ethyl acetate).

EXAMPLE 2

2-[3-[3-(Piperidinomethyl)phenoxy]propylamino]-3-chloropyridine

3-[3-(Piperidinomethyl)phenoxy]propylamine (2.17 g) and 2,3-dichloropyridine (1.27 g) were dissolved in 3-methylpyridine (6 ml) and stirred under reflux for 16 hours. The majority of the reaction solvent was removed by vacuum distillation (120 torr, 70°-80° C.) and the residue was neutralised with aqueous potassium carbonate (5%; 40 ml), washed with water (2×100 ml) and extracted into chloroform (40 ml). The chloroform extract was evaporated under reduced pressure and subjected to column chromatography (chloroform:methanol 25:1) to give the title compound as an oil (1.15 g). This was treated with oxalic acid as in Example 1 to give 2-[3-[3-(piperidinomethyl)phenoxy]propylamino]-3/chloropyridine dioxalate (1.1 g), m.p. 154–155° C.

EXAMPLE 3

2-[3-[3-(Piperidinomethyl)phenoxy]propylamino]quinoline

3-[3-(Piperidinomethyl)phenoxy]propylamine (2.0 g) and 2-chloroquinoline (1.31 g) were fused at 140° C. for two hours. The oily residue was taken up in methanol/water (5:50), neutralised with solid potassium carbonate and extracted into chloroform. The chloroform extract was dried, evaporated under reduced pressure and subjected to medium pressure liquid chromatography (chloroform) to afford the title product as an oil (0.77 g). This was treated with maleic acid to give 2-[3-[3-(piperidinomethyl)phenoxy]propylamino]quinoline dimaleate (0.4 g), m.p. 148°14 150° C. (recrystallised from ethanol).

EXAMPLE 4

2-[3-[3-(Piperidinomethyl)phenoxy]propylamino]pyrimidine

3-[3-(Piperidinomethyl)phenoxy]propylamine (2.0 g) and 2-chloropyrimidine (0.92 g) were fused at 160° C. for one hour. The reaction mixture was worked-up in a manner similar to that of Example 3 to give the title compound as an oil. This was treated with oxalic acid to give 2-[3-[3-(piperidinomethyl)phenoxy]propylamino]pyrimidine dioxalate (0.8 g), m.p. 181°-183° C. (recrystallised from methanol).

EXAMPLE 5

2-[3-[3-(Piperidinomethyl)phenoxy]propylamino]benzthiazole

3-[3-(Piperidinomethyl)phenoxy]propylamine (7.0 g) and 2-chlorobenzthiazole (5.26 g) were dissolved in dichloromethane to ensure good mixing. The solvent was then evaporated and the residue fused at 130° C. for 16 hours. The cooled reaction mixture was subjected to chromatography on silica (chloroform:methanol 10:1)

to give the title compound as an oil (8.5 g). This was treated with maleic acid in isopropanol to give 2-[3-[3-[3-(piperidinomethyl)phenoxy]propylamino]benzthiazole dimaleate, m.p. 113° C. (decomp) (recrystallised from ethylacetate and isopropanol-ethyl acetate).

EXAMPLE 6

2-[3-[3-(Piperidinomethyl)phenoxy]propylamino]pyridine

3-[3-(Piperidinomethyl)phenoxy]propylamine (20 g) and 2-bromopyridine (12.64 g) were stirred at 125° C. for 3½ days. The cooled reaction mixture was subjected to column chromatography on silica ((chloroform:methanol 10:1) to afford the title compound as an oil. This was treated with maleic acid in ethanol to give, on addition of diethyl ether, as a white solid 2-[3-[3-(piperidinomethyl)phenoxy]propylamino]pyridine dimaleate (11.40 g), m.p. 116°–167° C. (recrystallised from isopropanol).

EXAMPLE 7

2-[3-[3-(Piperidinomethyl)phenoxy]propylamino]-6-methoxypyridine

3-[3-(Piperidinomethyl)phenoxy]propylamine (14.90 g) and 2-bromo-6-methoxypyridine (5.64 g) were heated with stirring in an oil bath at 165°–170° C. for 5 hours. The reaction mixture was cooled, dissolved in dilute hydrochloric acid to pH 3–4, washed with ether (5 times), taken to pH 9–10 with dilute sodium hydroxide, extracted into ether (5 times). The pH was adjusted after each extraction. The latter ether extracts were combined, dried (MgSO$_4$), evaporated under reduced pressure, and subjected to medium pressure chromatography on silica using ethyl acetate as eluant, to yield the title compound as an oil (2.45 g). This was treated with maleic acid in ethanol to give 2-[3-[3-(piperidinomethyl)phenoxy]propylamino]-6-methoxypyridine dimaleate (2.71 g), m.p. 114.5°–115° C.

EXAMPLE 8

2-[3-[3-(Piperidinomethyl)phenoxy]propylamino]-4-ethoxyquinoline

3-[3-(Piperidinomethyl)phenoxy]propylamine (9.93 g) and 2-chloro-4-ethoxyquinoline (4.15 g) were fused at 160° C. for 4¼ hours. The reaction mixture was cooled, dissolved in dilute hydrochloric acid to pH 6 and washed with diethyl ether (2×). The solution was taken to pH 5 and extracted continuously into chloroform. The chloroform extract was evaporated under reduced pressure, dissolved in water, taken to pH 9 with aqueous sodium hydroxide and extracted into diethyl ether (7×) and chloroform (2×). The ether and chloroform extracts were dried (MgSO$_4$) and evaporated to give the title compound as an oil (7.92 g). This was treated with maleic acid in ethanol to give 2-[3-[3-(piperidinomethyl)phenoxy]propylamino]-4-ethoxyquinoline dimaleate (8.24 g), m.p. 145.5°–147.5° C. (recrystallised from ethanol).

EXAMPLE 9

2-[3-[3-(Piperidinomethyl)phenoxy]propylamino]-thiazole

3-[3-(Piperidinomethyl)phenoxy]propylamine (7.45 g) and 2-bromothiazole (2.46 g) in pyridine (25 ml) were stirred under reflux for 20 hours. The reaction mixture was cooled, evaporated and partitioned between chloroform and water. The chloroform layer was evaporated and subjected to medium pressure column chromatography on silica (chloroform:methanol 19:1) to give the title compound as an oil. This was converted to 2-[3-[3(piperidinomethyl)phenoxy]propylamino]-thiazole dihydrochloride, m.p. 192.5°–193.5° C. (recrystallised from isopropanol-ethyl acetate).

EXAMPLE 10

2-[3-[3-(Piperidinomethyl)phenoxy]propylamino]-1-methylbenzimidazole

3-[3-(Piperidinomethyl)phenoxy]propylamine (2.41 g) and 1-methyl-2-methylthiobenzimidazole (1.57 g) were fused at 150° C. for 6 hours. The cooled residue was subjected to column chromatography on silica (chloroform:methanol 19:1) to give the title compound as an oil. This was treated with maleic acid to give 2-[3-[3-(piperidinomethyl)phenoxy]propylamino]-1-methylbenzimidazole dimaleate (0.87 g), m.p. 153°–154° C. (recrystallised from isopropanol).

EXAMPLE 11

3-[3-[3-(Piperidinomethyl)phenoxy]propylamino]pyridine (i) 3-[3-(Piperidinomethyl)phenoxy]propionic acid (UK Patent Application No. 2047238A) as the hydrochloride (3.0 g) was suspended in dichloromethane (70 ml) and treated with dimethylformamide (15 drops) and thionyl chloride (4.73 g). The solution was stirred at room temperature for 2 hours, evaporated and the residue dissolved in anhydrous dimethylformamide (35 ml). This solution was added slowly, with stirring, to 3-aminopyridine (0.94 g) in dimethylformamide (35 ml), subsequently triethylamine (2.18 g) was added and the mixture was stirred for 5 hours and then allowed to stand overnight. The solution was poured on to water (220 ml) taken to pH 9 and extracted into ethyl acetate (3×100 ml). The organic extracts were combined, dried, evaporated and the residue treated with petroleum ether (40°–60° C.) to give as a light-buff solid, 3-[3-[3-(piperidinomethyl)phenoxy]propionamido]pyridine (1.21 g), m.p. 92–96° C.

(ii) The product from part (i) above (1.19 g) in tetrahydrofuran (80 ml) was added slowly to a stirring suspension of lithium aluminium hydride (0.80 g) in tetrahydrofuran (60 ml). The mixture was stirred under reflux for 2½ hours, cooled and the excess hydride was destroyed. The mixture was filtered, evaporated, dissolved in dichloromethane (100 ml), washed with water, dried and evaporated to give the title compound as an oil. This was treated with maleic acid in isopropanol to give 3-[3-[3-(piperidinomethyl)phenoxy]propylamino]pyridine dimaleate (1.55 g), m.p. 120.5°–122° C. (recrystallised from isopropanol).

EXAMPLE 12

1-[3-[3-(Piperidinomethyl)phenoxy]-propylamino]isoquinoline

3-[3-(Piperidinomethyl)phenoxy]propylamine (2.04 g) and 1-methylsulphonylisoquinoline (1.70 g) were fused at 135° C. for 5¼ hours. The cooled reaction mixture was taken up in methanol, filtered, evaporated and subjected to medium pressure column chromatography on silica (chloroform:methanol 1:19-second column using chloroform) to give the title compound (0.56 g) as an oil. This was treated with maleic acid (0.35 g) in warm ethanol to yield, on cooling, 1-[3-[3-

(piperidinomethyl)phenoxy]propylamino]isoquinoline dimaleate (0.15 g), m.p. 103°–105° C. (recrystallised from ethanol).

EXAMPLE 13

2-[3-[3-(Piperidinomethyl)phenoxy]propylamino-4-benzyloxypyridine (i) 3-[3-(Piperidinomethyl)phenoxy]propylamine 6.21 g), 2-chloro-4-nitropyridine-N-oxide (4.36 g) and triethylamine (6.32 g) were stirred, in ethanol (30 ml), under reflux for 3½ hours. The reaction mixture was cooled gradually to 0° C. to yield 2-[3-[3-(piperidinomethyl)phenoxy]propylamino]-4-nitropyridine-N-oxide (4.23 g), m.p. 90°–90.5° C.

In an alternative method the 0.8 hydrobromide/0.2 hydrochloride salt of the above N-oxide may be prepared as below.

3-[3-(Piperidinomethyl)phenoxy]propylamine (16.67 g, 0.047 mol), 2-bromo-4-nitropyridine-N-oxide (9.91 g, 0.0453 mol) and triethylamine (14 ml, 0.10 mol) were stirred under reflux in ethanol (90 ml) for 6 hours. Ethanol was removed under reduced pressure to give an oil which was dissolved in 2N-hydrochloric acid to give a solution of pH 3 (adjustment with 2N-sodium hydroxide solution necessary). The solution was exhaustively extracted with chloroform, and the combined, dried chloroform layers were concentrated under reduced pressure to an oily solid, which was left under a small amount of methanol overnight. Resultant yellow crystals (11.7 g, 56%) were filtered and washed with cold methanol to give 2-[3-[3-(piperidinomethyl)phenoxy]propylamino]-4-nitropyridine-N-oxide 0.8 hydrobromide-0.2 hydrochloride, m.p. 197°–198° C. (recrystallised from ethanol).

(ii) Benzylalcohol (0.99 g, 0.95 ml, 0.0092 mol) was added dropwise to a suspension of sodium hydride (0.37 g, 0.0076 mol) (50% dispersion in oil) in dimethylformamide (20 ml) at room temperature under nitrogen. The mixture was stirred at room temperature for 30 minutes then 2-[3-[3-(piperidinomethyl)phenoxy]propylamino-4-nitropyridine-N-oxide (as 0.8 hydrobromide-0.2 hydrochloride salt) (1.4 g, 0.003 mol) suspended in dimethylformamide (30 ml) was added. To the dark blue mixture (containing anion) was therefore added more benzyl alcohol (5 ml, excess) and the mixture heated to 80° C. for 2 hours. After this time reaction was still incomplete, but was completed 5 minutes after addition of sodium hydride (0.37 g., 0.0076 mol).

The brown solution was poured into water (250 ml), extracted with ethyl acetate (3×50 ml) and the combined extracts were washed with a little water and extracted into 2N-hydrochloric acid (3×35 ml). The acid extracts were washed with ethyl acetate (50 ml) and adjusted to pH 10 with 50% sodium hydroxide solution then re-extracted into ethyl acetate (3×25 ml). The combined organic extracts were washed with brine, dried and concentrated under reduced pressure to give, as a brown gum-like solid, 2-[3-[3-(piperidinomethyl)phenoxy]propylamino]-4-benzyloxypyridine-N-oxide, (1.1 g). Recrystallisation from dichloromethane/4-0-60° C. petroleum ether gave 2-[3-[3-(piperidinomethyl)-phenoxy]propylamino-4-benzyloxypyridine-N-oxide.

In a similar manner the 4-nitropyridine-N-oxide free base (1.55 g) was converted to the 4-benzyloxypyridine-4-oxide (1.1 g), m.p. 143°–145.5° C. (recrystallised from dichloromethane/40°-60° C. petroleum ether).

(iii) Part of the product from (ii) above (1.10 g) in ethanol (100 ml) was subjected to hydrogenation at 345 kPa (50 p.s.i.) in the presence of Raney nickel (approx. 0.1 g). After 5 hours the reaction mixture was filtered and washed with ethanol. The filtrate was evaporated under reduced pressure to give 2-[3-[3-(piperidinomethyl)phenoxy]propylamino-4-benzyloxypyridine (1.07 g) as an oil. This was dissolved in ether and treated with maleic acid in ethanol to give the dimaleate salt (1.08 g), m.p. 145.5°–147.5° C. (recrystallised from ethanol).

EXAMPLE 14

2-[3-[3-(Piperidinomethyl)phenoxy]propylamino]-4,5-dimethylthiazole (i) Thionyl chloride (23.8 g) was added slowly to a cooled (0° C.) mixture of 3-[3-(piperidinomethyl)phenoxy]propionic acid and dimethylformamide (0.5 ml) in dichloromethane (100 ml). The resulting suspension was stirred at room temperature overnight, and solvent was removed under reduced pressure to give 3-[3-(piperidinomethyl)phenoxy]propionyl chloride hydrochloride (18.9 g) as an oil.

(ii) Part of the product from (i) (4.1 g), 2-amino-4,5-dimethylthiazole hydrochloride (2.12 g) and triethylamine (20 ml) in dimethylformamide (30 ml) was stirred for 4 hours at room temperature, allowed to stand overnight and then partitioned between chloroform and water. The chloroform layer was washed with water, dried and evaporated to yield a black oil, which was subjected to column chromatography on silica using chloroform:methanol (10:1) as eluant to give 2-[3-[3-(piperidinomethyl)phenoxy]propionamido]-4,5-dimethylthiazole (0.45 g).

(iii) A solution of the product from part (ii) (0.45 g) in dry tetrahydrofuran (20 ml) was added slowly to a stirring suspension of lithium aluminium hydride (0.46 g) in tetrahydrofuran (70 ml) and the resulting mixture was stirred at room temperature for one hour. Aqueous ammonium chloride was added dropwise until effervescence had ceased, followed by the addition of ethyl acetate. The resulting mixture was filtered and the ethyl acetate layer was washed with water, dried and evaporated to give a green oil, which was subjected firstly to column chromatography on silica using diethyl ether: 33% ethylamine in ethanol (50:1) as eluant, and secondly to preparative high performance column chromatography using 50% acetonitrile in aqueous ammonium acetate (0.1M) as eluant. The desired fractions from the preparative column were combined, evaporated to ca ⅓ volume and extracted with chloroform. The chloroform extracts were dried and evaporated to give the title compound as an oil. This was treated with maleic acid in isopropanol to give after recrystallisation from isopropanol/ethyl acetate, as white crystals, 2-[3-[3-piperidinomethyl)phenoxy]propylamino]-4,5-dimethylthiazole dimaleate (52 mg), m.p. 123°–125° C.

EXAMPLE 15

2-[5-[3-(Piperidinomethyl)phenoxy]pentylamino]benzthiazole 5-(3-(Piperidinomethyl)phenoxy]pentylamine (0.8 g) and 2-chlorobenzthiazole (0.53 g) were fused at 140° C. for 3 hours. The cooled residue was subjected to medium pressure column chromatography on silica using ethyl acetate as eluant to give the title compound as an oil. This was converted to 2-[5-[3-piperidinomethyl)-phenoxy]pentylamino]benzthiazole dihydrochloride (0.18 g), m.p. 140°–145° C. (recrystallised from ethanol/ether).

EXAMPLE 16

2-[2-[3-(Piperidinomethyl)phenoxy]ethylamino]benzthiazole (i) A mixture of 3-(piperidinomethyl)phenol (7 g), chloroacetonitrile (2.77 g) and potassium carbonate (5.06 g) in dry acetone (100 ml) was stirred under reflux overnight. The reaction mixture was filtered and the filtrate was evaporated to give a residue which was subjected to column chromatography on silica using chloroform:methanol (20:1) as eluant to afford 3-(piperidinomethyl)phenoxyacetonitrile (5.6 g).

(ii) A filtered solution of the product from (i) (5.6 g) in dry diethyl ether (600 ml) was added dropwise over 2 hours to a stirred suspension of lithium aluminium hydride (1.06 g) in diethyl ether (100 ml). The resulting mixture was allowed to stand overnight and excess hydride was destroyed by the dropwise addition of aqueous ammonium chloride until effervescence had ceased. The mixture was filtered and evaporated to give 2-[3-(piperidinomethyl)phenoxy]ethylamine (5.11 g).

(iii) Part of the product from (ii) (2.52 g) and 2-chlorobenzthiazole were fused at 100° C. for 4 hours and then at 125° C. for 4 hours. The cooled residue was subjected to column chromatography on silica using dichloromethane:methanol:ammonium hydroxide (90:5:0.5) as eluant to give the title compound. This was treated with maleic acid in isopropanol to give 2-[2-[3-(piperidinomethyl)phenoxy]ethylamino]benzthiazole dimaleate (1.47 g), m.p. 141°–142° C. (recrystallised from isopropanol/ethylacetate).

EXAMPLE 17

2-[4-[3-(Piperidinomethyl)phenoxy]butylamino]benzthiazole

In a similar manner to that of Example 16 (ii) reaction of 4-[3-(piperidinomethyl)phenoxy]butyronitrile (2.58 g) and lithium aluminium hydride (0.46 g) gave 4-[3-(piperidinomethyl)phenoxy]butylamine (2.55 g) as an oil. This oil and 2-chlorobenzthiazole (1.81 g) were fused at 130° C. for 4 hours. The cooled residue was subjected to column chromatography on silica using dichloromethane:methanol:ammonium hydroxide (90:5:05) as eluant to give the title compound (1.6 g), m.p. 92°–93° C. (recrystallised from toluene).

EXAMPLE 18

2-[3-[3-(Piperidinomethyl)phenoxy]propylamino]-3-methoxypyridine

3-[3-(Piperidinomethyl)phenoxy]propylamine (3.97 g) and 2-bromo-3-methoxypyridine (1.50 g) were heated with stirring at 100° C. for 48 hours. The cooled residue was partitioned between chloroform and water. The aqueous layer was further extracted with chloroform and the combined chloroform layers were washed with water, dried and evaporated to dryness. The brown residue was dissolved in aqueous acetic acid to pH 4 and extracted with ether to remove unreacted 2-bromo-3-methoxypyridine. The aqueous solution was basified with potassium carbonate to pH 9–10 and then extracted with chloroform. The combined chloroform extracts were washed, dried and evaporated to dryness. The residue was subjected to column chromatography on silica with chloroform as eluant to afford the title compound as an oil. This was treated with maleic acid in isopropanol to give as a white solid, 2-[3-[3-(piperidinomethyl)phenoxy]propylamino]-3-methoxypyridine dimaleate (0.82 g), m.p. 111°–112° C. (recrystallised from acetone-ethyl acetate).

EXAMPLE 19

4-[3-[3-(Piperidinomethyl)phenoxy]propylamino]quinazoline

3-[3-(Piperidinomethyl)phenoxy]propylamine (2.48 g) and 4-chloroquinazoline (1.64 g) were stirred in acetone (30 ml) at room temperature for 7 days. The acetone was evaporated and the oily residue was dissolved in 2 Normal hydrochloric acid. The acidic solution was extracted with ethyl acetate. The aqueous solution was then basified to pH 9 and was extracted with ethyl acetate. A solid crystallised from the basic ethyl acetate extract and was collected and dissolved in chloroform. The chloroform solution was washed with water, dried and evaporated to dryness. The residue was recrystallised from ethyl acetate to yield the title compound (0.6 g), m.p. 111° C.

EXAMPLE 20

4-[3-[3-(Piperidinomethyl)phenoxy]propylamino]quinoline

3-[3-(Piperidinomethyl)phenoxy]propylamine (13.51 g) and 4-chloroquinoline (4.45 g) were heated with stirring at 155° C. for 2½ hours. The cooled reaction mixture was dissolved in 2 Normal hydrochloric acid to pH 3–4 and the acidic solution was extracted with ethyl acetate. The aqueous solution was then basified to pH greater than 9 and was extracted with chloroform several times. The combined chloroform extracts were dried and evaporated to dryness to give the title compound as an oil. This was treated with maleic acid in ethanol to afford 4-[3-[3-(piperidionomethyl)phenoxy]propylamino]quinoline dimaleate (8.9 g), m.p. 127°–127.5° C. (recrystallised from isopropanol).

EXAMPLE 21

2-[3-[3-(Dimethylaminomethyl)phenoxy]propylamino]benzthiazole

3-[3-(Dimethylaminomethyl)phenoxy]propylamine (2.38 g) and 2-chlorobenzthiazole (1.94 g) were fused at 130° C. for 2 hours. The cooled residue was subjected to column chromatography on silica using chloroform followed by chloroform:methanol (25:1) as eluants to give the title compound as a yellow oil. This was converted to 2-[3-[3-(dimethylaminomethyl)phenoxy]propylamino]benzthiazole dihydrochloride (0.37 g), m.p. 154°–155° C. (recrystallised from ethanol/ether).

EXAMPLE 22

2-[3-[3-(Pyrrolidinomethyl)phenoxy]propylamino]benzthiazole

3-[3-(Pyrrolidinomethyl)phenoxy]propylamine (2.0 g) and 2-chlorobenzthiazole (1.45 g) were fused at 130° C. for 2½ hours. The cooled reaction mixture was subjected to column chromatography on silica using chloroform and then chloroform:methanol (10:1) as eluants to give the title compound as a yellow oil. This was treated with maleic acid in ethanol to give 2-[3-[3-(pyrrolidinomethyl)phenoxy]propylamino]benzthiazole dimaleate (0.35 g), m.p. 91°–92° C. (recrystallised from isopropanol/ether).

EXAMPLE 23

2-[3-[3-(Hexahydroazepinomethyl)phenoxy]-propylamino]benzthiazole

In a similar manner to that of Example 22 the product of the reaction of 3-[3-(hexahydroazepinomethyl)-phenoxy]propylamine and 2-chlorobenzthiazole was treated with maleic acid to give 2-[3-[3-(hexahydroazepinomethyl)phenoxy]propylamino]benzthiazole dimaleate (0.86 g), m.p. 112°–113° C. (recrystallised from ethanol/ether).

EXAMPLE 24

2-[3-[3-(Piperidinomethyl)phenoxy]propylamino]-5,6-dimethylbenzthiazole (i) A slurry of 2-amino-5,6-dimethylbenzthiazole (3.33 g) in glacial acetic acid (35 ml) was added slowly to a cooled (below 20° C.) solution of sodium nitrite in concentrated sulphuric acid (20 ml) with constant stirring. The reaction mixture was stirred for ½ hour, whilst the temperature was maintained below 20° C. Ether (300 ml) was added slowly and the resultant mixture was stirred at 0° C. for one hour. A precipitate was collected which was added directly to a cold solution of cuprous chloride (1.85 g) in hydrochloric acid (5N, 70 ml). The mixture was neutralised by the addition of potassium carbonate and a resultant brown precipitate was collected. This was subjected to column chromatography on silica using chloroform as eluant to give 2-chloro-5,6-dimethylbenzthiazole (273 mg), m.p. 175° C.

(ii) The product from (i) (273 mg) and 3-[3-piperidinomethyl)phenoxy]propylamine (343 mg) were fused at 140° C. for 6 hours. The residue was taken up in chloroform and the solution was washed with water, dried and evaporated to give a solid. This solid was subjected to column chromatography on silica using dichloromethane:methanol:ammonium hydroxide, (90:5:0.5) as eluant to give 2-[3-[3-(piperidinomethyl)-phenoxy]propylamino]-5,6-dimethylbenzthiazole (237 mg), m.p. 126°–127° C. (recrystallised from ethanol).

EXAMPLE 25

4(5)-[2-[3-(Piperidinomethyl)phenoxy]ethyl]imidazole 3-(Piperidinomethyl)phenol (2 g), 4(5)-[2-(bromo)ethyl]imidazole hydrobromide (1.6 g) and potassium carbonate (2.7 g) were stirred under reflux in acetone (20 ml) for 24 hours. Acetone was evaporated under reduced pressure to leave an oily residue which was subjected to column chromatography twice (chloroform:methanol:ammonia solution 95:5:1 as the first eluant and ethylacetate:methanol 95:5 as the second) to give the title compound as an oil. This was treated with oxalic acid to give 4(5)-[2-[3-(piperidinomethyl)phenoxy]ethyl]imidazole dioxalate, m.p. 187°–190° C. (recrystallised from ethanol-water).

EXAMPLE 26

2-[2-[3-(Piperidinomethyl)phenoxy]ethyl]-1H-benzimidazole

3-[3-(Piperidinomethyl)phenoxy]propionitrile (1.5 g), EP-A-87274, was dissolved in chloroform (30 ml), cooled to 0° C., and methanol (0.84 g) added. Dry hydrogen chloride gas was bubbled into the solution for 3 hours. The solution was allowed to stand at low temperature overnight, and evaporated under reduced pressure to leave as an oily residue, methyl 3-[3-(piperidinomethyl)phenoxy]propylimidate hydrochloride (3.77 g) which was not isolated. This was taken up in ethanol (20 ml) followed by the addition of ortho phenylenediamine (1.16 g) and stirred at room temperature for 2 hours. The mixture was evaporated under reduced pressure to leave an oily residue which was taken up in water, neutralised with potassium carbonate and extracted into chloroform (3×50 ml), which was dried over magnesium sulphate. The drying agent was filtered off, the volume of the chloroform was reduced and the solution was subjected to medium pressure liquid chromatography (ethyl acetate) to yield the title compound as a solid (0.21 g), m.p. 123°–125° C. (recrystallised from ethyl acetate).

EXAMPLE 27

2-[3-[3-(Piperidinomethyl)phenoxy]propyl]-1H-benzimidazole

Methyl 4-[3-(piperidinomethyl)phenoxy]butyrimidate hydrochloride (5.3 g) was prepared by the method of Example 8 of EP-A-87274 and not isolated. This was then taken up in ethanol (50 ml) followed by the addition of ortho-phenylenediamine (1.5 g) and stirred at room temperature for 2 hours. Ethanol was removed under reduced pressure to leave an oily residue which was dissolved up in water neutralised with potassium carbonate and extracted into chloroform (2×25 ml). The chloroform layer was dried over magnesium sulphate, filtered, evaporated to low volume under reduced pressure and the solution was subjected to medium pressure liquid chromatography (ethyl acetate) to afford the title compound as a solid, m.p. 115°–117° C. (recrystallised from ethyl acetate).

EXAMPLE 28

2-[4-[3-(Piperidinomethyl)phenoxy]butyl]1H-benzimidazole

5-[3-(Piperidinomethyl)phenoxy]pentanenitrile (1.73 g was dissolved in chloroform (20 ml). This solution was cooled to 0° C., which was followed by the addition of methanol (0.81 g). Dry hydrogen chloride gas was bubbled into the solution for 3 hours, which was then stored at 0° C. overnight. Chloroform was removed under reduced pressure to leave as an oily residue methyl 5-[3-(piperidinomethyl)phenoxy]pentaneimidate hydrochloride (1.3 g) which was not isolated. This was taken up in ethanol (20 ml) followed by the addition of orthophenylenediamine (0.41 g) and stirred at room temperature for 2 hours. Ethanol was removed under reduced pressure to leave an oily residue which was taken up in water, neutralised with potassium carbonate and extracted into chloroform (3×50 ml) and dried over magnesium sulphate, filtered, evaporated to low volume under reduced pressure and subjected to medium pressure liquid chromatography (ethyl acetate) to afford the title compound as a solid, m.p. 130°–131° C. (recrystallised from ethyl acetate).

EXAMPLE 29

3(5)-[2-[3-(Piperidinomethyl)phenoxy]ethyl]pyrazole

A mixture of 3-(piperidinomethyl)phenol, 3(5)-[2-(bromo)ethyl]pyrazole hydrobromide and potassium carbonate in acetone is heated to afford the title compound.

EXAMPLE 30

A pharmaceutical composition for oral administration is prepared containing:

| | | % by weight |
|---|---|---|
| A | 2-[3-(3-(piperidinomethyl)phenoxy)-propylamino]benzthiazole dimaleate | 55 |
| | Dibasic calcium phosphate dihydrate | 20 |
| | Approved colouring agent | 0.5 |
| | Polyvinylpyrrolidone | 4.0 |
| B | Microcrystalline Cellulose | 8.0 |
| | Maize Starch | 8.0 |
| | Sodium glycollate | 4.0 |
| | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, can be formulated into pharmaceutical compositions by a similar procedure.

DESCRIPTION 1

2-[3-[3-(Piperidinomethyl)phenoxy]propylamino]benzimidazole

2-[3-[3-(Piperidinomethyl)phenoxy]propylamino]-benzimidazole, m.p. 146°-8° C., was prepared from 3-[3-(piperidinomethyl)phenoxy]propylamine and 2-chlorobenzimidazole in a manner similar to that of U.S. Pat. No. 4,447,611.

BIOLOGICAL TEST METHODS AND DATA

The histamine $H_2$-antagonist activity of the compounds of this invention can be demonstrated by the inhibition of histamine-induced tachycardia in the isolated guinea-pig right atrium.

In the guinea pig atrium test a spontaneously beating isolated portion of the guinea pig right atrium is secured under tension (300 mg) between an anchorage and a transducer in a 15 ml tissue bath and immersed in Mc-Ewens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity ($pA_2$ value).

In the above test representative compounds for use in the compositions of this invention gave the following data:

| | $pA_2$ |
|---|---|
| Compound of Example 1 | 7.2 |
| Compound of Example 3 | 6.2 |
| Compound of Example 4 | 5.7 |
| Compound of Example 5 | 7.6 |
| Compound of Example 6 | 6.1 |
| Compound of Example 7 | 6.1 |
| Compound of Example 8 | 5.7 |
| Compound of Example 9 | 7.4 |
| Compound of Example 10 | 5.1 |
| Compound of Example 12 | 6.4 |
| Compound of Example 14 | 5.6 |
| Compound of Example 16 | 5.2 |
| Compound of Example 17 | 6.9 |
| Compound of Example 18 | 6.2 |
| Compound of Example 19 | 7.7 |
| Compound of Example 21 | 5.9 |
| Compound of Example 22 | 7.0 |
| Compound of Example 23 | 6.5 |
| Compound of Example 24 | 4.6 |
| Compound of Example 25 | 4.6 |
| Compound of Example 26 | 4.7 |
| Compound of Example 27 | 6.5 |
| Compound of Example 28 | 6.9 |
| Compound of Description 1 | 7.2 |

The brain histamine $H_2$-receptor affinity for representative compounds for use in the compositions of this invention can be demonstrated by ligand binding studies according to the method of Gajtkowski et al (Nature, vol 304, p 65 (1983)). Inhibition of $^3H$-tiotidine binding to guinea pig cerebral cortex membranes by the compounds gave inhibition constants (Ki) from which the following data are obtained:

| | pKi cortex |
|---|---|
| Compound of Example 1 | 7.1 |
| Compound of Example 3 | 7.9 |
| Compound of Example 4 | 5.5 |
| Compound of Example 5 | 7.1 |
| Compound of Example 6 | 7.0 |
| Compound of Example 7 | 6.3 |
| Compound of Example 8 | 6.7 |
| Compound of Example 9 | 7.2 |
| Compound of Example 10 | 7.5 |
| Compound of Example 11 | 6.1 |
| Compound of Example 12 | 7.4 |
| Compound of Example 14 | 6.9 |
| Compound of Example 16 | 6.1 |
| Compound of Example 17 | 6.8 |
| Compound of Example 18 | 7.4 |
| Compound of Example 19 | 7.6 |
| Compound of Example 21 | 6.2 |
| Compound of Example 22 | 6.5 |
| Compound of Example 23 | 5.9 |
| Compound of Example 24 | 6.4 |
| Compound of Example 25 | 6.1 |
| Compound of Example 26 | 5.4 |
| Compound of Example 27 | 7.0 |
| Compound of Example 28 | 7.4 |
| Compound of Description 1 | 7.6 |

Brain histamine $H_2$-receptor affinity can also be demonstrated by inhibition of dimaprit (a specific $H_2$-receptor agonist) stimulated cyclic AMP accumulation in guinea pig hippocampal slices according to the method of Palacios et al (Molecular Pharmacology, 14, 971 (1978)).

|  | pKi |
| --- | --- |
| Compound of Example 1 | 7.66 |
| Compound of Example 3 | 7.97 |
| Compound of Example 4 | 4.64 |
| Compound of Example 5 | 7.80 |
| Compound of Example 6 | 7.25 |
| Compound of Example 9 | 7.2 |
| Compound of Example 10 | 8.70 |
| Compound of Description 1 | 7.43 |

The anticonvulsant activity of a compound of this invention can be demonstrated by showing antagonism of experimentally-induced convulsions in mice, for example those produced by maximal electroshock and those following the injection of leptazol (pentylenetetrazol). The compound of Example 6 protected against maximal electroshock seizures at doses of 30–100 mg/Kg subcutaneously, and against leptazol-induced tonic extensor spasm in a dose-dependent manner over the range 30–100 mg/Kg subcutaneously. The compound of Example 5 protected against maximal electroshock seizures at doses of 30–100 mg/Kg subcutaneously, and against leptazol-induced tonic extensor spasm in a dose-dependent manner over the range 10–30 mg/Kg subcutaneously. The compound of Example 1 protected against maximal electroshock seizures at doses of 30–100 mg/Kg subcutaneously, and against leptazol-induced tonic extensor spasm at 10–100 mg/Kg subcutaneously.

Using the cat pial artery in situ experimental paradigm (for example, see Edvinsson et al, J. Pharmac. exp. ther., 225, 168–175 (1983)), it has been shown that locally applied cimetidine antagonises the pial artery dilation induced by perivascular application of histamine (Wahl & Kuschinsky, Circ. Res. 44, 161–165 (1979)). Intravenous cimetidine failed to antagonise this effect of histamine. The compound of Example 5 applied either locally or intravenously antagonised the pial artery dilatation induced by perivascularly-applied histamine.

Representative compounds for use in the compositions of this invention are demonstrated to cross the blood-brain barrier by a test method involving rats anaesthetised with urethane. Radiolabelled compound at doses designed to give approximately 2 μM blood concentrations, together with counter labelled inulin as a blood marker, is given as an intravenous bolus and then an intravenous infusion via the lateral tail vein. The levels of compound and inulin in the blood are monitored and the infusion maintained for at least 2 hours until equilibria (or at least approximate blood plateaux) are achieved. The rat is exsanguinated to minimise blood contamination of the brain. The brain is removed, quickly rinsed in saline and dissected on refrigerated glass plate, using the method of Glowinski and Iversen (1966). The tissues are weighed and then dissolved in a tissue solubiliser, e.g. Soluene-100 overnight at 37° C. in glass vials. (Ratio 1 ml Soluene to 150 mg tissue). Glacial acetic acid is added to each vial in order to neutralise the soluene and reduce chemiluminescence. Dimilume-30 (15 ml) is added as the scintillant and the vials left for 12 hours in the scintillation counter in order to further reduce chemiluminescence prior to counting for activity. The assayed inulin is used to correct for residual blood in the brain, as inulin does not cross the blood-brain barrier and remains exclusively in the blood. The molar ratio of compound in the brain to compound in the blood is then calculated so that the higher the number the greater the ability of the compound to cross the blood-brain barrier.

The compound of Example 6 gave values of 6.5 and 4.7 in two separate determinations. The compound of Example 1 gave values of 108 and 1.4, the compound of Example 5 gave values of 0.8, 1.2, 1.8 and 2.0 in four separate experiments and the compound of Example 9 gave values of 2 and 3.6. For comparison cimetidine gave values of 0.04 and 0.01 and ranitidine is not detected above background $^{14}C$ levels. Imipramine, a CNS-acting antidepressant gives a value of 3.5.

(* Soluene-100 is a tissue solubiliser and is a trademark of United Technologies Packard. Dimilume-30 is a scintillant and is a trademark of United Technologies Packard).

The compounds described in Examples 5 and 6 had log P octanol/water values of 1.46 and 2.88 respectively indicating that the compounds are significantly lipophilic. In comparison cimetidine has a value of 0.4.

We have found that the ability of the compounds to penetrate the blood-brain barrier can be assesed by measurement of their Δ log P values. Δlog P is defined as the difference between log P octanol/water and log P cyclohexane/water. The compounds described in Examples 5 and 6 had Δlog P values of 1.74 and 1.07 respectively. The Δ log P value for cimetidine is greater than 3. An accurate comparative Δ log P value for cimetidine is not available since the cyclohexane/water partition coefficient for cimetidine is extremely low to be readily measurable.

What is claimed is:

1. A compound of the formula (I):

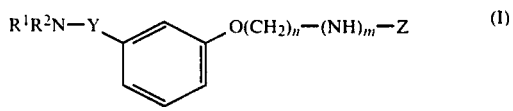

or a pharmaceutically acceptable salt thereof, wherein:

$R^1$ and $R^2$ are independently $C_{1-4}$alklyl; or $R^1$ and $R^2$ together with the nitrogen atom to which they are joined represent a pyrrolidino, piperidino or hexahydroazepino ring;

Y is a straight-chain or branched-chain $C_{1-4}$alkyl;

n is 2 to 5;

m is 1;

Z is:

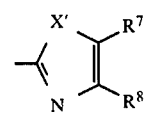

wherein

X' is oxygen, or sulphur;

$R^7$ and $R^8$ are independently hydrogen, $C_{1-6}$alkyl, phenyl, benzyl, halo, benzyloxy or $C_{1-4}$alkoxy; or $R^7$ and $R^8$ may be joined to form a benzene ring; said benzene ring being optionally substituted by up to 3 moieties selected from $C_{1-6}$alkyl, $C_{1-6}$alkoxy, halo, phenyl, benzyl or benzyloxy;

with the proviso that when X' is oxygen $R^7$ and $R^8$ are independently $C_{1-6}$alkyl, phenyl, hydrogen or benzyl, or are joined to form an optionally substituted benzene ring.

2. A compound according to claim 1 wherein n is 3.

3. A compound according to claim 1 or 2 wherein $R^1R^2N$-Y- is piperidinomethyl.

4. A compound according to claims 1 or 2 wherein $R^7$ and $R^8$ are independently hydrogen.

5. A compound according to claim 1 or 2 wherein $R^7$ and $R^8$ are joined to form a benzene ring.

6. A compound according to claims 1 or 2 wherein X' is a sulphur atom and $R^7$ and $R^8$ are joined to form a benzene ring.

7. A compound according to claim 1 which is: 2-[3-[3-(piperidinomethyl)phenoxyl]propylamino]benzoxazole or a pharmaceutically acceptable salt thereof.

8. A compound according to claim 1 which is: 2-[3-[3-(piperidinomethyl)phenoxy]propylamino]benzthiazole or a pharmaceutically acceptable salt thereof.

9. A compound according to claim 1 which is: 2-[3[3-(piperidinomethyl)phenoxy]propylyamino]thiazole or a pharmaceutically acceptable salt thereof.

10. A compound according to claim 1 which is: 2-[3-[3-(piperidinomethyl)phenoxy]propylamino]-4,5-dimethylthiazole or a pharmaceutically acceptable salt thereof.

11. A compound according to claim 1 which is: 2-[5-[3-(piperidinomethyl)phenoxy]pentylamino]benzthiazole or a pharmaceutically acceptable salt thereof.

12. A compound according to claim 1 which is: 2-[2-[3-(piperidinomethyl)phenoxy]ethylamino]benzthiazole or a pharmaceutically acceptable salt thereof.

13. A compound according to claim 1 which is: 2-[4-[3-(piperidinomethyl)phenoxy]butylamino]benzothiazole.

14. A compound according to claim 1 which is: 2-[3-[3-(dimethylaminomethyl)phenoxy]propylamino]benzthiazol e or a pharmaceutically acceptable salt thereof.

15. A compound according to claim 1 which is: 2-[3-[3-(pyrrolidinomethyl)phenoxy]propylamino]benzthiazole or a pharmaceutically acceptable salt thereof.

16. A compound according to claim 1 which is: 2-[3-[3-(hexahydroazepinomethyl)phenoxy]propylamino]benzthiazole or a pharmaceutically acceptable salt thereof.

17. A compound according to claim 1 which is: 2-[3-[3-(piperidinomethyl)phenoxy]propylamino]-5,6-dimethylbenzthiazole or a pharmaceutically acceptable salt thereof.

18. A pharmaceutical composition for blocking histamine $H_2$-receptors which comprises an effective amount of a compound according to claim 1 and a pharmaceutically acceptable carrier.

19. A pharmaceutical composition for blocking histamine $H_2$-receptors in the brain which comprises an effective amount of a compound according to claim 1 and a pharmaceutically acceptable carrier.

* * * * *

UNITED STATES PATENT AND TRADEMARK OFFICE
CERTIFICATE OF CORRECTION

PATENT NO. : 4,681,883

DATED : July 21, 1987

INVENTOR(S) : Thomas H. Brown; Robert C. Mitchell; Ian R. Smith; and Rodney C. Young It is certified that error appears in the above-identified patent and that said Letters Patent is hereby corrected as shown below:

Claim 13, lines 5-6: "benzothiazole" should read -- benzthiazole -- .

Signed and Sealed this

Eighth Day of December, 1987

Attest:

DONALD J. QUIGG

*Attesting Officer*  *Commissioner of Patents and Trademarks*